United States Patent [19]

Mack et al.

[11] Patent Number: 5,530,044
[45] Date of Patent: Jun. 25, 1996

[54] ALKYL END-CAPPED, HALOGENATED POLYETHERS

[75] Inventors: Arthur G. Mack, Lafayette; Enrico J. Termine, West Lafayette, both of Ind.

[73] Assignee: Great Lakes Chemical Corporation, West Lafayette, Ind.

[21] Appl. No.: 438,694

[22] Filed: May 11, 1995

[51] Int. Cl.$^6$ .................................................... C08K 5/06
[52] U.S. Cl. ............................................ 524/366; 524/368
[58] Field of Search ........................................ 524/366, 368

[56] References Cited

U.S. PATENT DOCUMENTS

| | | |
|---|---|---|
| 4,032,508 | 6/1977 | Anderson . |
| 5,414,046 | 5/1995 | Davis . |
| 5,420,183 | 5/1995 | Arena et al. .......................... 524/120 |

Primary Examiner—Shelley A. Dodson
Attorney, Agent, or Firm—Woodard, Emhardt, Naughton, Moriarty & McNett

[57] ABSTRACT

Fire-retardant tetrabromobisphenol oligomers of the formula:

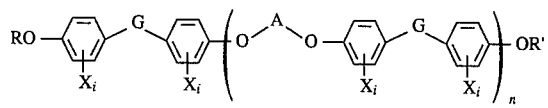

R or R' is a branched or unbranched alkyl radical;

$X_i$ is a halogen, wherein i is an integer from 0 to 4;

G is a connecting group selected from the group consisting of a single bond, a branched or unbranched divalent aliphatic hydrocarbon radical of from 1 to 10 carbon atoms, oxygen, sulfur, sulfoxide, $SO_2$, or oxygen-, silicon-, sulfur- or nitrogen-containing aliphatic hydrocarbon radicals such as —OR"O—, —OR"OR"O—, —SR"S—, —SR"SR"S—, —OSiR$_2$O—, —OSiR$_2$OSiR$_2$O—, O$_2$C—R"—CO$_2$, CO$_2$—R"—O$_2$C, SO—R"—SO—, SO$_2$—R"—SO$_2$,
wherein R" is a divalent aliphatic hydrocarbon radical;

A is a branched or unbranched alkyl diradical; and n is 0 or a positive integer.

The fire-retardant tetrabromobisphenol oligomers of the present invention are advantageous due to their non-reactive end-caps.

13 Claims, No Drawings

ALKYL END-CAPPED, HALOGENATED POLYETHERS

FIELD OF THE INVENTION

The present invention relates generally to polyethers, and more particularly to novel alkyl end-capped halogenated polyether compounds.

BACKGROUND OF THE INVENTION

Novel compositions of matter comprising halogenated polyethers have been prepared. In general, halogenated compounds are known to be fire retardants for plastics. For example compounds such as tetrabromobisphenol-A, tetrabromobisphenol-A bis(2,3-dibromopropyl ether), 1,2-dibromoethane/ 4,4'-isopropylidene bis(2'6-dibromophenol) copolymer and brominated epoxy resins impart flame retardancy on plastics into which they are compounded. Yet compounds which have greater stability and better fire retardancy are sought.

Previously known compounds such as tetrabromobisphenol-A, tetrabromobisphenol-A bis(2,3-dibromopropyl ether), 1,2 -dibromoethane/4,4'-isopropylidene bis(2'6-dibromophenol) copolymer, or brominated epoxy resins are used as flame retardant additives in materials such as polystyrene, high impact polystyrene; copolymers of styrene; polycarbonates; polyurethanes; polyimides; polyamides; polyethers; acrylics; polyesters; epoxies; phenolics; elastomers such as butadiene/styrene copolymers and butadiene/acrylonitrile copolymers; terpolymers of acrylonitrile, butadiene and styrene; natural rubber; butyl rubber and polysiloxanes. Additional representative polymers include those of olefinically saturated monomers such as ethylene, propylene and butadiene; copolymers of two or more such alkylene monomers; copolymers of one or more such alkylene monomers, etc. Blends of polymers may also be used. By virtue of the invented materials having aromatic bromine they will impart flame retardancy to the polymer to which they are added as it is well known that brominated molecules act as flame retardants.

The aforementioned, previously known compounds possess reactive groups which can lead to degradation in the compounded plastic. The alkyl end-caps and repeating units of the invention are inert compared to the end-caps and repeating units of the known materials. Additionally, as the invented materials are oligomeric, the desired property of broad melt range is imparted which is known to allow easy compounding. Thus, it is the object of this invention to provide novel compositions of matter possessing desirable physical characteristics of flame proofing and fire retardancy and retaining the property of easy compounding, imparting good physical properties to the resin while avoiding undesirable instability.

A need therefore exists for fire-retardant, halogenated polyethers that do not contain reactive end groups and that thus avoid the problems associated with prior art compounds. The present invention addresses that need.

SUMMARY OF THE INVENTION

Briefly describing one aspect of the present invention, there are provided halogenated polyethers of the formula:

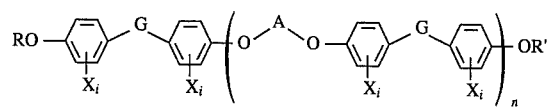

wherein each

R or R' is a branched or unbranched alkyl radical;

$X_i$ is a halogen, preferably Br, wherein i is an integer from 1 to 4;

G is a connecting group selected from the group consisting of a single bond, a branched or unbranched divalent aliphatic hydrocarbon radical of from 1 to 10 carbon atoms, oxygen, sulfur, sulfoxide, $SO_2$, or oxygen-, silicon-, sulfur- or nitrogen-containing aliphatic hydrocarbon radicals such as —OR"O—, —OR"OR"O—, —SR"S—, —SR"SR"S—, —OSiR$_2$O—, —OSiR$_2$OSiR$_2$O—, $O_2$C—R"—$CO_2$, $CO_2$—R"—$O_2$C, SO—R"—SO—, $SO_2$—R"—$SO_2$, wherein R" is a divalent aliphatic hydrocarbon radical;

A is a branched or unbranched alkyl diradical; and n is 0 or a positive integer.

One object of the present invention is to provide end-capped, halogenated polyethers that avoid the problems associated with prior art compositions.

Further objects and advantages of the present invention will be apparent from the following description.

DESCRIPTION OF THE PREFERRED EMBODIMENT

For the purpose of promoting an understanding of the principles of the invention, reference will now be made to preferred embodiments and specific language will be used to describe the same. It will nevertheless be understood that no limitation of the scope of the invention is thereby intended, such alterations and further modifications in the illustrated embodiments, and such further applications of the principles of the invention as illustrated herein being contemplated as would normally occur to one skilled in the art to which the invention pertains.

As previously indicated, the present invention relates generally to polyethers with non-reactive end caps. In particular, the inventive compositions are polyethers of the formula:

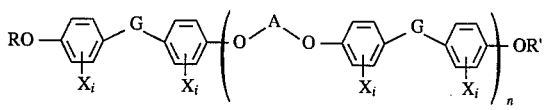

where:

R or R' is a branched or unbranched alkyl radical;

$X_i$ is a halogen, preferably Br, wherein i is an integer from 0 to 4;

G is a connecting group selected from the group consisting of a single bond, a branched or unbranched divalent aliphatic hydrocarbon radical of from 1 to 10 carbon atoms, oxygen, sulfur, sulfoxide, $SO_2$, or oxygen-, silicon-, sulfur- or nitrogen-containing aliphatic hydrocarbon radicals such as —OR"O—, —OR"OR"O—, —SR"S—, —SR"SR"S—, —OSiR$_2$O—, —OSiR$_2$OSiR$_2$O—, O$_2$C—R"—CO$_2$, CO$_2$—R"—O$_2$C, SO—R"—SO—, SO$_2$—R"—SO$_2$, wherein R" is a divalent aliphatic hydrocarbon radical;

A is a branched or unbranched alkyl diradical; and n is 0 or a positive integer.

In certain preferred embodiments G is a connecting group of the formula —CYY'— where Y and Y' are aliphatic hydrocarbon radicals and in particular methyl radicals.

In some preferred embodiments A is a divalent hydrocarbon radical having from 1–10 carbon atoms.

The compounds of the present invention are useful as flame-retardants, particularly when compounded with other plastic compositions. The compounds are less subject to decomposition. Accordingly, the flame-retarded plastics are more resistant to deterioration of color, loss of plasticity, etc., which may result when prior art polyethers are used.

The halogenated polyethers of the present invention are particularly useful as flame retardant additives in materials such as polystyrene, high impact polystyrene; copolymers of styrene; polycarbonates; polyurethanes; polymides, polyamides; polyethers; acrylics; polyesters; epoxies, phenolics; elastomers such as butadiene/styrene copolymers and butadiene/acrylonitrile copolymers; terpolymers of acrylonitrile, butadiene and styrene; natural rubber; butyl rubber and polysiloxanes. Additional representative polymers include those of olefinically saturated monomers such as ethylene, propylene and butadiene; copolymers of two or more such alkylene, propylene and butadiene; copolymers of two or more such alkylene monomers; copolymers of one or more such alkylene monomers, etc. Blends of polymers may also be used.

The compounds of the above formula may be prepared by reacting a tetrahalo-bisphenol of the formula:

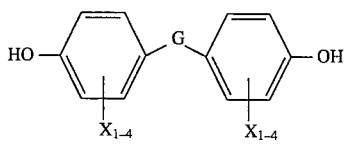

with a divalent reactant, for example ethylene dibromide, in the presence of base in a polar solvent such as propylene glycol. The reaction mixture is heated to about 100° C. for a period of at least about 4–5 hours. At this point, an alkyl halide or dialkyl sulfate is added and heating is continued until a drop in the temperature of the reaction indicates that the reaction between the phenolic sodium salt and the alkylating agent is essentially complete.

The average molecular weight of the oligomeric mixtures produced by the above reactions can be tailored by adjusting the stoichiometry of the initial dihaloalkane to halogenated bisphenol dianion mixture. Chain length can also be modified by appropriate choice of the dihalo- and/or haloalkane. In one preferred embodiment the average molecular weight of the oligomeric mixture lies in the range 1500 to 6000 most preferably between about 1500 and 2500. In certain preferred embodiments the average chain length of the oligomeric mixture is between about 1 and 4.

Reference will now be made to specific examples using the processes described above. It is to be understood that the examples are provided to more completely describe preferred embodiments, and that no limitation to the scope of the invention is intended thereby.

EXAMPLE 1

Ppreparation of Methyl End-Capped Tetrabromobisphenol-A/Ethylene Dibromide Oligomers (n=2)

A three-liter round bottom flask was charged with 543.7 g tetrabromobisphenol A (TBBPA) and 1 kg propylene glycol and the resulting slurry was heated to 80° C. A charge of 127.4 g sodium carbonate was added portionwise to the reactor followed by 2.4 g sodium metabisulfite. The resulting mixture was heated to 100° C. and was allowed to react for 15 minutes. From a dropping funnel, 140.9 g ethylene dibromide was added as quickly as possible and the mixture was allowed to react at 100° C. for 280 minutes. Methyl bromide was added to the reaction mixture through a dip-tube until uptake ceased and the reaction mixture's temperature dropped to 83° C. Reflux was maintained for 60 minutes. The product was separated from the reaction mixture by pumping the hot mixture into three times its volume of water and decanting off the solvent mixture. The product was taken up in toluene and the solution was washed with several portions of water. Residual water was removed by azeotropic distillation and residual salt removed by filtration. Toluene was removed by rotary evaporation to a final temperature of 155° C. at 1 mm Hg. A sample of the light amber glass thus obtained was ground with mortar and pestle and analyzed.

The material thus obtained had the following physical and chemical characteristics:

Organic Bromine (OBr)=57.2%

Glass transition by differential scanning calotimetry (tg)= 63.2° C.

Softening range (S.R.)=81°–94° C.

EXAMPLE 2

Preparation of Methyl End-Capped Tetrabromobisphenol-A/Ethylene Dibromide Oligomers (Average n=2)

A three-liter round bottom flask was charged with 543.7 g TBBPA and 1 kg propylene glycol and the resulting slurry was heated to 100° C. A charge of 127.4 g sodium carbonate was added portionwise to the reactor followed by 2.5 g sodium metabisulfite. The resulting mixture was heated to 100° C. and was allowed to react for 45 minutes. From a dropping funnel, 125.2 g ethylene dibromide was added as quickly as possible and the mixture was allowed to react at 100° C. for 250 minutes. Methyl bromide was added to the reaction mixture through a dip-tube until uptake ceased and the reaction mixture's temperature dropped to 75° C. Reflux was maintained for 60 minutes. The crude product was separated from the reaction mixture by precipitation from water and decanting off the solvent mixture. The product was taken up in toluene and the solution was washed with several portions of water. Residual water was removed by azeotropic distillation and residual salt removed by filtration. Toluene was removed by rotary evaporation to a final temperature of 150° C. at 20 mm Hg. A sample of the light amber glass thus obtained was ground with mortar and pestle and analyzed. Data obtained are as follows:

OBr=58.5% $t_g$=59.7° C. S.R.=79°–87° C.

EXAMPLE 3

Preparation of Methyl End-Capped Tetrabromobisphenol-A/Ethylene Dibromide Oligomers (Average n=4)

A 600 ml autoclave was charged with 135.9 g TBBPA, 150 g dimethoxyethane, 120 g water, 2.0 g sodium metabisulfite, 37.6 g dibromoethane, and 58.2 g sodium carbonate. The reactor was sealed and heated at 100° C. for 24 hours. After cooling to 0° C., 51.6 g methylbromide was charged to the reactor. After 5 days the reactor was vented and the contents transferred to a one-liter round bottom flask and diluted with 500 ml toluene. Water was removed by azeotropic distillation. After filtration of the salts from the mixture the solvents were removed by rotary evaporation to 145° C. at 10 mm Hg. Data obtained are as follows:

OBr=54.2% $t_g$=130° C. S.R.=139°–172° C.

EXAMPLE 4

Preparation of Butyl End-Capped Tetrabromobisphenol-A/Butylene Dibromide Oligomers (Average n=2)

A one-liter round bottom flask was charged with 135.9 g TBBPA and 250 g propylene glycol and the resulting slurry was heated to 90° C. A charge of 31.8 g sodium carbonate was added portionwise to the reactor followed by 0.66 g sodium metabisulfite. After 165 minutes a charge of 36.0 g 1,4-dibromobutane was added to the reaction mixture and the temperature was elevated to 115° C. and the mixture allowed to react for 165 minutes. The mixture was cooled to 85° C. and 27.6 g 1-bromobutane was added to the reactor. During the course of the final reaction 100 ml 1,4-dioxane was added to maintain dissolution of the product. The product was separated from the reaction mixture by decanting off the solvent mixture. The product was taken up in toluene and the solution was washed with water. Residual water was removed by azeotropic distillation and residual salt removed by filtration. Toluene was removed by rotary evaporation to a final temperature of 165° C. at 10 mm Hg affording a 56.6% yield. A sample of the light amber glass thus obtained was ground with mortar and pestle and analyzed. Data obtained are as follows:
OBr=52.2%
S.R.=163°–193° C.

EXAMPLE 5

Preparation of Methyl End-Capped Tetrabromobisphenol-A/Ethylene Dibromide Oligomers (Average n=2)

A three-liter round bottom flask was charged with 652.3 g TBBPA and 1.5 kg cyclohexanone and the resulting slurry was heated to 127° C. for 30 minutes. From a droping funnel, 169.1 g ethylene dibromide was added as quickly as possible and the mixture was allowed to react at 100° C. for 7 hours. Over a period of 2 hours 189.6 g methyl bromide was added to the reaction mixture through a dip-tube. The reaction mixture was filtered (to remove salts) into 1500 ml of 90° C. water. The two phase system was stirred and then phase separated. The organic phase was stripped at 175° C. and 0.5 mm Hg. The amber glass thus obtained gave the following analysis:

OBr=56.7% tg=56.2° C. S.R.=87°–185° C.

EXAMPLE 6

Preparation of Methyl End-Capped Tetrabromobisphenol-S/Ethylene Dibromide Oligomers (Average n=3)

A 500 ml round bottom flask was charged with 133.2 g tetrabromobisphenol S and 248 g cyclohexanone and the resulting slurry was heated to 123° C. A charge of 25.4 g sodium carbonate was added portionwise to the reactor. The resulting mixture was react at 123° C. for 15 minutes. From a dropping funnel, 28.2 g ethylene dibromide was added as quickly as possible and the mixture was allowed to react at 123° C. for 8 hours. The reactor was cooled to 80° C. and 2 bromopropane was added as quickly as possible to the reaction. The temperature was raised to 105° C. and allowed to react for 8 hours.

The reaction mixture was cooled to room temperature and was poured into seven times its volume of methanol in order to precipitate the product. The solvent was decanted from the product and the semisolid product was stripped of residual solvent by rotary evaporation to a final temperature of 175° C. at ca. 20 mm Hg. The tan solid thus obtained was pulverized and analyzed. Data obtained are as follows:

OBr=54.66% tg=53.5° C. S.R.=243–305 dec.)° C.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A composition of the formula:

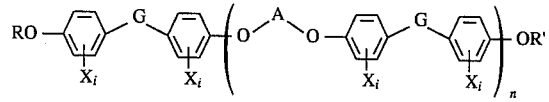

wherein

R or R' is a branched or unbranched alkyl radical;

$X_i$ is a halogen, wherein i is an integer from 1 to 4;

G is a connecting group selected from the group consisting of a single bond, a branched or unbranched divalent aliphatic hydrocarbon radical of from 1 to 10 carbon atoms, oxygen, sulfur, sulfoxide, $SO_2$, or oxygen-, silicon-, sulfur- or nitrogen-containing aliphatic hydrocarbon radicals such as —OR"O—, —OR"OR"O—, —SR"S—, —SR"SR"S—, —OSiR$_2$O—, —OSiR$_2$OSiR$_2$O—, $O_2$C—R"—$CO_2$, $CO_2$—R"—$O_2$C, SO—R"—SO—, $SO_2$—R"—$SO_2$, wherein R" is a divalent aliphatic hydrocarbon radical;

A is a branched or unbranched alkyl diradical having from 1 to 10 carbon atoms; and n is 0 or a positive integer.

2. A composition according to claim 1 in which X represents bromine or chlorine radicals in the 2,2',6, and 6' ring positions.

3. A composition according to claim 1 in which X is Br.

4. A composition according to claim 1 in which R and R' are methyl radicals.

5. A composition according to claim 1 in which G is a branched or unbranched divalent hydrocarbon radical having from 1–10 carbon atoms.

6. A composition according to claim 5 in which G is an isopropylidene diradical.

7. A composition according to claim 1 in which A is a 1,2-ethyl diradical.

8. A composition according to claim 7 in which n is between 0 and 4.

9. A composition according to claim 1 in which X is bromine in the 2,2',6, and 6' ring positions; R and R' are methyl radicals; G is an isopropylidene diradical; A is a 1,2-ethyl diradical; and n is between 0 and 10.

10. A composition according to claim 1, said composition being a methyl end-capped tetrabromobisphenol A/ethylene dibromide oligomer with an average n=3.

11. A composition according to claim 1, said composition being a methyl end-capped tetrabromobisphenol A/ethylene dibromide oligomer with an average n=2.

12. A composition according to claim 1, said composition being a methyl end-capped tetrabromobisphenol A/ethylene dibromide oligomer with an average n=4.

13. A composition according to claim 1, said composition being a methyl end-capped tetrabromobisphenol A/butylene dibromide oligomer with an average n=2.

* * * * *

UNITED STATES PATENT AND TRADEMARK OFFICE
CERTIFICATE OF CORRECTION

PATENT NO. : 5,530,044
DATED : June 25, 1996
INVENTOR(S) : Arthur G. Mack and Enrico J. Termine It is certified that error appears in the above-indentified patent and that said Letters Patent is hereby corrected as shown below:

In col. 4, line 2, please change "Ppreparation" to --Preparation--.

In col. 6, line 16, please change "dec.)°" to --(dec.)°--.

Signed and Sealed this

Eighth Day of October, 1996

BRUCE LEHMAN

*Attest:*

*Attesting Officer*        *Commissioner of Patents and Trademarks*